US012751458B2

(12) United States Patent
Chang et al.

(10) Patent No.: US 12,751,458 B2
(45) Date of Patent: Oct. 6, 2026

(54) COATING COMPOSITION COMPRISING BACTERIOPHAGE AND ANTIBACTERIAL FILM FORMED BY USING SAME

(71) Applicant: Kookmin University Industry Academy Cooperation Foundation, Seoul (KR)

(72) Inventors: Yoonjee Chang, Seoul (KR); Sang Bin Kim, Gunpo-si (KR)

(73) Assignee: Kookmin University Industry Academy Cooperation Foundation, Seoul (KR)

( * ) Notice: Subject to any disclaimer, the term of this patent is extended or adjusted under 35 U.S.C. 154(b) by 537 days.

(21) Appl. No.: 18/040,518

(22) PCT Filed: Jul. 13, 2022

(86) PCT No.: PCT/KR2022/010203

§ 371 (c)(1),
(2) Date: Feb. 3, 2023

(87) PCT Pub. No.: WO2023/146038

PCT Pub. Date: Aug. 3, 2023

(65) Prior Publication Data

US 2024/0254340 A1 Aug. 1, 2024

(30) Foreign Application Priority Data

Jan. 28, 2022 (KR) ........................ 10-2022-0013071
Apr. 14, 2022 (KR) ........................ 10-2022-0046236

(51) Int. Cl.
*C09D 5/14* (2006.01)
*A01N 63/40* (2020.01)
(Continued)

(52) U.S. Cl.
CPC ............ *A01N 63/40* (2020.01); *B65D 81/28* (2013.01); *C08J 5/18* (2013.01); *C08K 5/053* (2013.01);
(Continued)

(58) Field of Classification Search
None
See application file for complete search history.

(56) References Cited

FOREIGN PATENT DOCUMENTS

CN 108588037 A 9/2018
JP 2021-165368 A 10/2021
(Continued)

OTHER PUBLICATIONS

Radford, D., et al., "Characterization of antimicrobial properties of *Salmonella* phage Felix O1 and Listeria phage A511 embedded in xanthan coatings on Poly(lactic acid) films", Food Microbiology, vol. 66, pp. 117-128. (Year: 2017).*
(Continued)

*Primary Examiner* — Grant C Currens
(74) *Attorney, Agent, or Firm* — Sughrue Mion, PLLC

(57) ABSTRACT

A coating composition contains a bacteriophage having a bactericidal activity against *Salmonella* bacteria, a polymeric compound, and a plasticizer. Thus, a coating having antibacterial activity may be prepared by using the coating composition, and the bacteriophage stably survives even after coating formation to continuously maintain excellent antibacterial activity. When the coating composition is applied to a coating or film for food packaging, it may effectively prevent food from being contaminated by *Salmonella* bacteria to improve food safety and shelf life.

16 Claims, 14 Drawing Sheets

(51) Int. Cl.

| | |
|---|---|
| ***B65D 81/28*** | (2006.01) |
| ***C08J 5/18*** | (2006.01) |
| ***C08K 5/053*** | (2006.01) |
| ***C09D 7/63*** | (2018.01) |
| ***C12N 7/00*** | (2006.01) |

(52) U.S. Cl.
CPC ................. *C09D 5/14* (2013.01); *C09D 7/63* (2018.01); *C12N 7/00* (2013.01)

(56) References Cited

FOREIGN PATENT DOCUMENTS

| | | | |
|---|---|---|---|
| KR | 10-2001-0101907 | A | 11/2001 |
| KR | 10-1007180 | B1 | 1/2011 |
| KR | 10-1072883 | B1 | 10/2011 |
| KR | 10-2015-0024116 | A | 3/2015 |
| KR | 10-2018-0071601 | A | 6/2018 |
| KR | 10-2018-0100533 | A | 9/2018 |
| KR | 10-2020-0008434 | A | 1/2020 |
| KR | 10-2237011 | B1 | 4/2021 |
| KR | 10-2021-0147972 | A | 12/2021 |
| WO | 2015/084938 | A1 | 6/2015 |

OTHER PUBLICATIONS

Chen et al., "Three *Salmonella enterica* serovar Enteritidis bacteriophages from the Siphoviridae family are promising candidates for phage therapy", Canadian Journal of Microbiology, vol. 64, pp. 865-875. (Year: 2018).*

Whichard et al., "Complete Genomic Sequence of Bacteriophage Felix O1", Viruses, vol. 2, pp. 710-730. (Year: 2010).*

Kim et al., "Evaluating the antibacterial efficacy of a polyvinyl alcohol film containing *Salmonella enteritidis* bacteriophage PBSE191", KoSFOST International Symposium and Annual Meeting, 2021, 2 pages.

Kim, "Development of a biodegradable and antimicrobial polyvinyl alcohol film loaded with a *Salmonella* virulent phage", Korea Society of Packaging Science and Technology, 2021, 6 pages.

Vincent Leung, et al., "Long-Term Antimicrobial Activity of Phage-Sugar Glasses is Closely Tied to the Processing Conditions", ACS Omega, 2018, vol. 3, pp. 18295-18303 (9 pages total).

Office Action issued May 7, 2024 in Japanese Application No. 2023-507502.

* cited by examiner

Wild-type

△*rfb*P mutant

△*rfb*P/LT2C · pUHE::*rfb*P (Bootstrap value: > 70%)

COATING COMPOSITION COMPRISING BACTERIOPHAGE AND ANTIBACTERIAL FILM FORMED BY USING SAME

CROSS REFERENCE TO RELATED APPLICATIONS

This application is a National Stage of International Application No. PCT/KR2022/010203 filed Jul. 13, 2022, claiming priorities based on Korean Patent Application No. 10-2022-0013071 filed Jan. 28, 2022, and Korean Patent Application No. 10-2022-0046236 filed Apr. 14, 2022.

TECHNICAL FIELD

The present invention relates to a coating composition comprising a bacteriophage and an antibacterial film prepared using the same, and more particularly, to a coating composition comprising a bacteriophage having a bactericidal activity against *Salmonella* bacteria and capable of preparing a coating having excellent stability and antibacterial activity of the bacteriophage, and an antibacterial film prepared using the composition.

BACKGROUND ART

Food is likely to be contaminated by pathogens during manufacturing, distribution, and storage, and when contaminated with bacteria, not only does food quality deteriorate, but food poisoning may occur when ingested. According to the statistics of the Ministry of Food and Drug Safety of Korea, the number of patients with food poisoning due to *Salmonella* infection during the period from 2017 to 2020 was reported to account for 33.5% of the total number of patients with food poisoning, and thus, it is important to prevent food contamination by pathogens such as *Salmonella* bacteria.

As a general technique for preventing food contamination by pathogens to ensure freshness and safety of food, there is a method of killing pathogens using antibiotics. However, antibiotics were difficult to show long-term effects due to the emergence of resistant bacteria, and thus, there was a need for research on antibacterial materials that can replace antibiotics.

As an alternative to antibiotics, techniques using natural antibacterial materials such as natural extracts and plant essential oils have been developed. For example, Korean Patent No. 10-1072883 describes materials for antibacterial coating and packaging using refined mustard oil. However, when natural materials were used, it was difficult to secure stable antibacterial activity and was disadvantageous in preserving the sensory properties of food, and there was a possibility of destroying the balance of the microbiome by removing beneficial bacteria.

As a material that can replace existing antibacterial substances such as the antibiotics and natural materials, a technology using a bacteriophage is attracting attention. Bacteriophage is a virus that uses bacteria as a host and is an antibacterial substance that binds to host bacteria to induce its death. In particular, bacteriophages have a characteristic of killing a specific category of bacteria and not affecting other bacteria. As an example, Korean Patent Application Laid-Open No. 10-2018-0100533 describes a bacteriophage having the ability to specifically kill *Pseudomonas aeruginosa*. According to these bacteria-specific characteristics, the use of bacteriophages may kill only the desired pathogen, and thus, there is an advantage that the problem of killing beneficial bacteria does not appear.

Bacteriophages are safe biomaterials that have been approved as generally recognized as safe (GRAS) by the U.S. Food and Drug Administration (FDA) since 2006, and have been applied to food additives to prevent food contamination by pathogens. However, when the bacteriophages are applied to the coating film, the survival rate of the bacteriophage in the coating is lowered due to the coating formation process and the materials used for the coating, and thus, there is a limitation that excellent antibacterial activity cannot be exhibited in the form of a coating. Accordingly, the use of bacteriophages is mainly limited to a solution or powder, and thus, there is a need for the development of a technology capable of controlling to secure the stability of bacteriophages and maintain excellent antibacterial activity against *Salmonella* even after coating formation.

DISCLOSURE

Technical Problem

It is an object of the present invention to provide a coating composition capable of preparing an antibacterial film having excellent survival rate and stability of bacteriophages.

It is another object of the present invention to provide an antibacterial film prepared using the coating composition.

It is another object of the present invention to provide a bacteriophage having the ability to specifically kill *Salmonella* spp. bacteria.

Technical Solution

In order to achieve the above objects, the present invention provides a coating composition comprising a bacteriophage having a bactericidal activity against *Salmonella* spp. bacteria, a polymeric compound, and a plasticizer.

In the present invention, the *Salmonella* spp. bacteria may comprise *Salmonella enterica*.

In the present invention, the *Salmonella* spp. bacteria may comprise one or more *Salmonella enterica* serotypes selected from the group consisting of *Salmonella* Enteritidis (S. Enteritidis), *Salmonella* Typhimurium (S. Typhimurium), *Salmonella* Paratyphi (S. Paratyphi), *Salmonella* Salamae (S. Salamae), *Salmonella* Diarizonae (S. Diarizonae), and *Salmonella* Dublin (S. Dublin).

In the present invention, the bacteriophage may belong to Siphoviridae.

In the present invention, the bacteriophage may be a bacteriophage deposited under Accession No. KCTC14929BP having a bactericidal activity specifically against *Salmonella* spp. bacteria.

In the present invention, the polymeric compound may comprise one or more selected from the group consisting of polyvinyl alcohol (PVA), polylactic acid (PLA), polycaprolactone (PCL), polybutylene succinate (PBS), polyethylene terephthalate (PET), polybutylene terephthalate (PBT), polyethylene (PE), polypropylene (PP), polyvinyl chloride (PVC), polyamide (PA), and polyurethane (PU).

In the present invention, the polymeric compound may comprise a biodegradable polymer.

In the present invention, the plasticizer may comprise one or more selected from the group consisting of sorbitol, glycerol, trehalose, fructose, sucrose, mannitol, propylene glycol, and polyethylene glycol.

In the present invention, the plasticizer may be in an amount of 10 to 30% by weight based on the weight of the polymeric compound.

In the present invention, the coating composition may further comprise a solvent.

In the present invention, the bacteriophage may be in an amount of $1\times10^8$ to $1\times10^{12}$ PFU/mL based on the total volume of the coating composition.

In the present invention, the polymeric compound may be in an amount of 5 to 20 g/100 mL based on the total volume of the coating composition.

In the present invention, the plasticizer may be in an amount of 1 to 5 g/100 mL based on the total volume of the coating composition.

The present invention also provides an antibacterial film prepared using the coating composition.

In the present invention, the antibacterial film may be prepared by coating the coating composition on a substrate and then drying it at a temperature of 20 to 30° C. for 10 to 20 hours.

In the present invention, the antibacterial film may be prepared by coating the coating composition on a subject to be coated and then drying it at a temperature of 20 to 30° C. for 10 to 180 minutes.

In the present invention, the antibacterial film may be a coating for food packaging.

The present invention also provides a bacteriophage deposited under Accession No. KCTC14929BP having the ability to specifically kill *Salmonella* spp. bacteria.

Advantageous Effects

The coating composition of the present invention comprises a bacteriophage having a bactericidal activity against *Salmonella* bacteria to exhibit antibacterial activity, and the bacteriophage may stably survive even after coating formation to continuously maintain excellent antibacterial activity. Accordingly, when the present invention is applied to a coating or film for food packaging, it may effectively prevent food from being contaminated by *Salmonella* bacteria to improve food safety and storage.

BEST MODE

Figure 1:
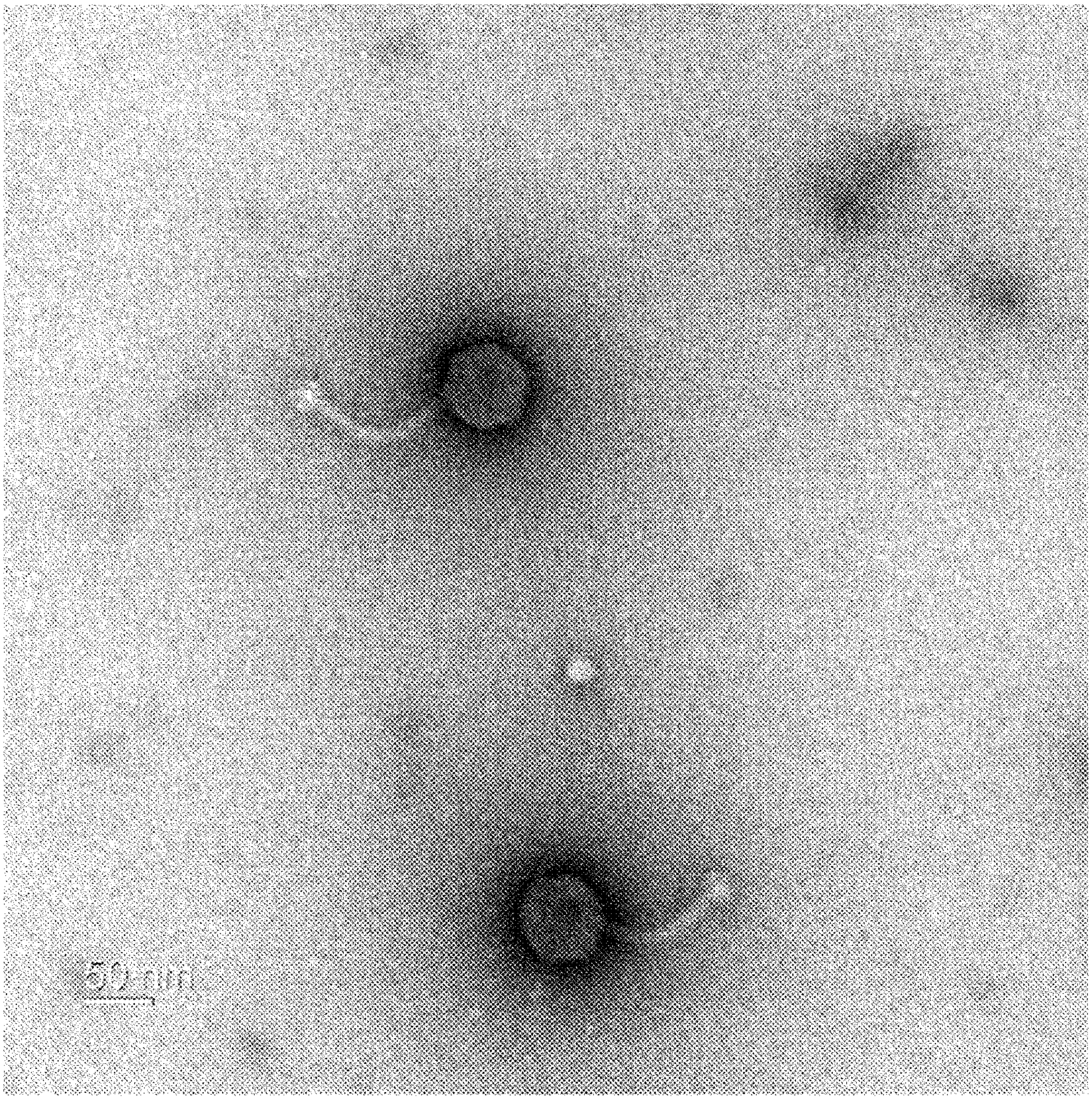
FIG. 1 shows a transmission electron microscope (TEM) picture of the isolated bacteriophage PBSE191 according to an embodiment of the present invention.

Hereinafter, specific embodiments of the present invention will be described in more detail. Unless defined otherwise, all technical and scientific terms used in the present specification have the same meaning as commonly understood by those of ordinary skill in the technical field to which the present invention pertains. In general, the nomenclature used in the present specification is those well known and commonly used in the art.

The present invention relates to a bacteriophage, a coating composition comprising the same, and an antibacterial film prepared using the same.

The coating composition of the present invention comprises bacteriophage thereby exhibiting antibacterial activity, and the bacteriophage may stably survive even after forming a coating or film using the same to exhibit continuous antibacterial activity. In addition, in the present invention, by using a bacteriophage having excellent bactericidal activity against *Salmonella* spp. bacteria, which is a food pathogen, and having high stability against heat and pH, an antibacterial film that may be usefully applied as a material for food coating or packaging may be provided.

Bacteriophage is a virus that uses bacteria as a host, and may be abbreviated as "phage". Bacteriophage kills host bacteria by a lytic cycle and/or a lysogenic cycle. For example, according to the lytic cycle, bacteriophage infects bacteria, proliferates inside the bacterial cells, and is released while destroying the cell wall of the host bacteria after proliferation to kill the bacteria. One type of bacteriophage has the ability to kill only a specific category of host bacteria, and thus, a bacteriophage may be selected according to the type of bacteria to be killed, or a new bacteriophage may be discovered and used.

The bacteriophage used in the present invention may have the ability to kill *Salmonella* spp. bacteria, which is a representative food pathogen. Accordingly, when the bacteriophage is applied to a material for food packaging, it exhibits an antibacterial activity that kills *Salmonella* bacteria and inhibits its reproduction, so that it may prevent food from being contaminated by *Salmonella* bacteria.

Specifically, the bacteriophage used in the present invention may have the ability to specifically kill *Salmonella enterica*, and in particular, may exhibit the ability to kill one or more serotypes selected from the group consisting of *Salmonella* Enteritidis (S. Enteritidis), *Salmonella* Typhimurium (S. Typhimurium), *Salmonella* Paratyphi (S. Paratyphi), *Salmonella* Salamae (S. Salamae), *Salmonella* Diarizonae (S. Diarizonae), and *Salmonella* Dublin (S. Dublin), among others.

In an embodiment of the present invention, the bacteriophage may be bacteriophage PBSE191 (hereinafter referred to as "phage PBSE191"). The phage PBSE191 has been deposited with the Korean Collection for Type Cultures at the Korea Research Institute of Bioscience and Biotechnology of 181, Ipsin-gil, Jeongeup-si, Jeollabuk-do 56212, Republic of Korea on 2 on Mar. 31, 2022 under Accession No. KCTC14929BP according to the Budapest Treaty On the International recognition of the Deposit of Microorganisms For the Purpose of Patent Procedure.

The phage PBSE191 belongs to Siphoviridae, and it was confirmed in an embodiment of the present invention that the phage PBSE191 exhibits antibacterial activity specifically against *Salmonella* spp. bacteria, particularly *Salmonella enterica*, and has excellent thermal stability and pH stability, thereby being able to be applied under various temperature and pH conditions. Accordingly, when the phage PBSE191 is applied to a material for food packaging, it may exhibit the excellent bactericidal activity against *Salmonella* bacteria, which is a food pathogen, thereby improving food safety and storage.

Accordingly, the present invention may provide a coating composition comprising a bacteriophage, more specifically, an antibacterial coating composition for food packaging comprising a bacteriophage. When the coating composition of the present invention is used, the survival rate and stability of bacteriophages are high even after coating formation, and thus, a film having excellent antibacterial activity may be prepared.

The coating composition of the present invention may comprise a bacteriophage, a polymeric compound, and a plasticizer.

The bacteriophage in the coating composition exhibits the bactericidal activity against bacteria as described above, and thus, a film having antibacterial activity may be prepared using the same.

In the present invention, the polymeric compound becomes a matrix of the coating, and may be polyvinyl alcohol (PVA), polylactic acid (PLA), polycaprolactone (PCL), polybutylene succinate (PBS), polyethylene terephthalate (PET), polybutylene terephthalate (PBT), polyethylene (PE), polypropylene (PP), polyvinyl chloride (PVC), polyamide (PA), polyurethane (PU), or the like. Among them, biodegradable polymers such as polyvinyl alcohol, polylactic acid, polycaprolactone and polybutylene succinate may be used. In particular, polyvinyl alcohol is harmless to the human body, biodegradable, and excellent in film formation and oxygen barrier properties, and thus, it may be preferably used for manufacturing materials for eco-friendly food packaging.

In the present invention, as the polyvinyl alcohol, polyvinyl alcohol having a weight average molecular weight (Mw) of 5,000 to 50,000, specifically 10,000 to 30,000, for example, 13,000 to 23,000 may be used, and polyvinyl alcohol having a degree of saponification of 80 to 95%, preferably 82 to 92%, for example, 87 to 89% may be used.

In the present invention, the plasticizer refers to an additive that is incorporated into a polymeric compound to control physical properties of a film. In general, when a bacteriophage is applied to a polymer coating, the bacteriophage is inactivated depending on the type of polymer or the coating process, resulting in a problem in that the antibacterial activity of the coating is lowered. Under these situations, the present inventors found that when the bacteriophage was applied to the coating film, the plasticizer not only could simply control the physical properties of the film, but also had an important effect on the survival rate of the bacteriophage, and have completed the present invention. According to the present invention, a coating film having very excellent antibacterial activity may be provided by using a plasticizer together with a bacteriophage and a polymeric compound and controlling the type and content thereof.

The plasticizer used in the present invention may include sorbitol, glycerol, trehalose, fructose, sucrose, mannitol, propylene glycol, polyethylene glycol, and the like, and preferably may include sorbitol. When sorbitol is used, the survival rate of bacteriophages may be high compared to other plasticizers after film formation to exhibit excellent antibacterial activity, and long-term stability may be secured to continuously maintain antibacterial activity.

In the present invention, the plasticizer may be included in an amount of 10 to 30% by weight, preferably 15 to 25% by weight, and more preferably 18 to 22% by weight based on the weight of the polymeric compound. Bacteriophages may stably survive to exhibit excellent antibacterial activity even after coating formation in the above content range, and if the content of the plasticizer is too low or high, the amount of bacteriophages killed during the coating formation process or after coating formation may increase, thereby lowering the antibacterial activity of the coating. In addition, if the content of the plasticizer is too low, the mechanical properties and oxygen barrier properties of the coating may be deteriorated, and even if the content of the plasticizer is too high, there is a concern about a decrease in strength and discoloration of the coating, and the solubility and moisture permeability are too high, and thus, it may be unsuitable for use as a material for food packaging.

The type and amount of plasticizer in the case of general polymer coatings were determined based on the desired properties of the coating, but the present invention has excellent technical significance in that when bacteriophage was introduced into the coating, the type and content of the plasticizer have been found to contribute to the survival rate and stability of bacteriophage, and an optimal composition capable of maximizing the activity and stability of bacteriophage has been found.

According to a preferred embodiment of the present invention, polyvinyl alcohol may be used as a polymeric compound, and sorbitol may be used as a plasticizer in a coating composition comprising the bacteriophage. In this case, optimal activity may be exhibited in terms of survival rate, long-term stability and antibacterial activity of bacteriophage after coating formation.

In terms of the survival rate and stability of bacteriophage, the content of the polymeric compound may be 5 to 20 g/100 mL, preferably 8 to 15 g/100 mL based on the total volume of the coating composition of the present invention, and the content of the plasticizer may be 1 to 5 g/100 mL, preferably 1.5 to 2.5 g/100 mL. In this case, the bacteriophage may be included in an amount of $1\times10^{8}$ to $1\times10^{12}$ PFU (plaque forming unit)/mL, for example, $1\times10^9$ to $1\times10^{10}$ PFU/mL, and specifically may in an amount of $2\times10^9$ to $8\times10^9$ PFU/mL.

The coating composition of the present invention may further comprise additives such as wetting agents and preservatives, if necessary. In addition, it may be used in the form of a solution by adding a solvent for coating, wherein the volume of the composition may be based on the total volume of the solution. As the solvent, water or an organic solvent may be used, and a suitable solvent may be used depending on the type of polymeric compound. For example, when polyvinyl alcohol is used, a coating solution may be prepared using water as a solvent.

Accordingly, the present invention may also provide an antibacterial film formed using the coating composition.

In the present invention, the antibacterial film may be prepared using the coating composition, that is, a coating composition comprising a bacteriophage, a polymeric compound, and a plasticizer. In this case, the coating composition may be used in the form of a solution containing a solvent for coating properties.

In the present invention, the film may be interpreted as meaning including a film in a form directly coated on a subject to be coated such as food (for example, eggs) or food containers, as well as a single film form.

Specifically, the antibacterial film may be formed by adding a bacteriophage to a solution containing a polymeric compound and a plasticizer, then coating the solution on a subject or substrate, and then drying it. In this case, the solution may be diluted for use, if necessary.

In the present invention, when the antibacterial film is directly formed on food or food containers, it may be formed by a method of spraying a solution on a subject or immersing the subject in the solution. For example, the film may be formed by coating the coating composition on a subject and then drying it at a temperature of 20 to 30° C. for 10 to 180 minutes.

Alternatively, when the antibacterial film is prepared as the single film form, it may be prepared using a method of coating a solution on a substrate by a method such as casting. For example, the film may be formed by coating the coating composition on a substrate under a relative humidity condition of 30 to 70 RH % and then drying it at a temperature of 20 to 30° C. for 10 to 20 hours.

By using the present invention, bacteriophage may stably survive even in the form of a film to exhibit excellent antibacterial activity. Therefore, when the present invention is applied to a material for food packaging, it may effectively prevent food from being contaminated by pathogens to improve food safety and storage.

EXAMPLES

Hereinafter, the present invention will be described in more detail through examples. However, these Examples show some experimental methods and configurations only for illustrating the present invention, and the scope of the present invention is not limited to these Examples.

Experimental Method

In the experiment, *Salmonella* Enteritidis ATCC 13076 was used as a host, and LB broth (MB-L4488; MB cell, Seoul, Korea), 0.5% (w/v) LB molten agar and 1.5% (w/v) LB agar medium (MB-L4487, MB cell) were used as a culture medium.

Phage titer was measured using a double-layer agar plate with 0.5% (w/v) LB molten agar and 1.5% (w/v) LB agar as the upper and lower layers, respectively.

Preparation Example 1: Purification, Propagation and Stock Preparation of Bacteriophages Bacteriophages (hereinafter referred to as "phages") were obtained from domestic sewage samples and purified through a double-layer agar assay and a plaque assay. One plaque was resuspended in phosphate buffered saline (PBS), centrifuged at 15,000×g for 1 minute at 4° C., and filtered through a sterile WHATMAN™ PVDF membrane filter with a pore size of 0.22 μm. The filtration process was repeated 5 times.

To propagate the isolated phage, the phage was cultured in LB broth using *S. enteritidis* ATCC 13076 as a host. Specifically, after subinoculation of S. Enteritidis ATCC 13076 with 1%, and the culture was incubated at 37° C. for 1.5 hours. Then, the phage was cultured at 37° C. for 4 hours under aerobic conditions. The sample was centrifuged at 15,000×g for 10 minute at 4° C., and the supernatant was filtered through a sterile WHATMAN™ PVDF membrane filter with a pore size of 0.45 μm. The above steps were performed sequentially for three volume conditions (3, 50 and 300 mL of cultured bacteria) to obtain a sufficient amount of phage lysate.

To obtain a higher titer phage stock, the purified phage lysate was centrifuged at 30,000×g for 30 minutes at 4° C. to obtain a pellet. For this, the phage concentration (PFU/mL) was measured using the double-layer agar assay. The purified phage was amplified to obtain a lysate having a titer of $10^{10}$ PFU/mL or more, and stored at 4° C. until use, and stored in 35% glycerol at −80° C. for long-term storage.

The phage isolated and purified according to the above method was named "phage PBSE191," was deposited with the Korean Collection for Type Cultures at the Korea Research Institute of Bioscience and Biotechnology, and was given Accession No. KCTC14929BP as of Mar. 31, 2022.

Experimental Example 1: Transmission Electron Microscope (TEM) Analysis of Phage For phage PBSE191, morphology was analyzed using transmission electron microscope (TEM).

A 200 mesh copper grid coated with formvar/carbon was pretreated with an electrical discharge machine (US/91000, USA). The phage was loaded on the copper grid, and then was negatively stained with 2% (v/v) uranyl acetate (pH 4.5). The sample was analyzed with an energy-filtering Libra 120 transmission electron microscope (Carl Zeiss, Germany), and the results are shown in FIG. 1.

Referring to the TEM image of FIG. 1, it can be confirmed that the phage PBSE191 has an icosahedral head and a flexible tail without contractility. Specifically, the head of the phage had an icosahedral shape with a particle diameter of 58.84±1.78 nm (n=13), a tail length of 115.06±5.64 nm (n=13), and a width of 10.13±0.91 nm (n=13).

The phage PBSE191 was similar to phages LPST94, BSPM4 and CGG3-1 in terms of structure, but had a shorter tail compared to the above phages. From the above results, it could be seen that the phage PBSE191 belongs to the family Siphoviridae of the order Caudovirales.

Experimental Example 2: Bacterial Challenge Assay Using Phage

A bacterial challenge assay was performed using *S. enteritidis* ATCC13076 and phage PBSE191.

The subcultured S. Enteritidis was cultured at 37° C. for 1.5 hours under aerobic conditions. Thereafter, phage infection was performed on the cultures under conditions of multiplicity of infection (MOI) of 0.01, 0.1, 1, 10 and 100, respectively. While growing the host at 37° C. for 9 hours under aerobic conditions, the absorbance at 600 nm was measured using a UV-visible spectrophotometer (SP-UV 300, Spectrum Instruments, Perkin Elmer, UK) to confirm lytic activity, and the above experiment was repeated 3 times.

Figure 2:
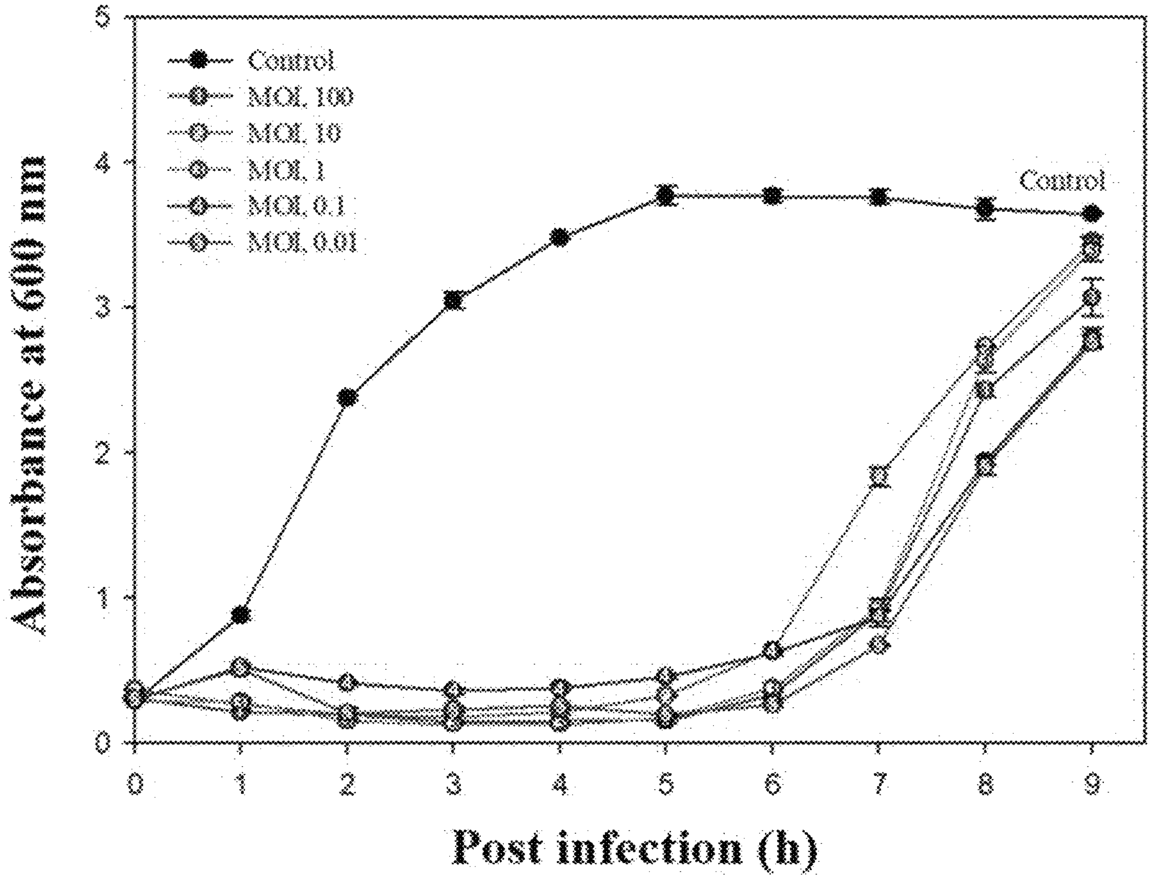
FIG. 2 is a graph showing the results of measuring the activity of bacteriophage PBSE191 according to an embodiment of the present invention to inhibit the growth of *Salmonella* bacteria.

FIG. 2 shows the results of measuring the activity to inhibit the growth of *Salmonella* bacteria in the presence of the phage. From the activity to inhibit the growth in FIG. 2, it was confirmed that the phage may rapidly inhibit the growth of S. Enteritidis. The results showed that the phages rapidly inhibited the growth of host bacterial cells within 1 hour under conditions of MOI of 100, 10, 1, 0.1 and 0.01 compared to the negative control group. In addition, the results showed that this inhibition of growth lasted for 6 hours in all experimental groups, and the phage exhibited higher lytic activity at high density to rapidly lyse the host bacteria and continuously inhibit the growth.

From the above results, it could be confirmed that the phage PBSE191 exhibited excellent and long-lasting bacterial lysis.

Experimental Example 3: Host Range Determination of Phage

A spot test was performed on the bacteria in Table 1 to determine the host range of the phage PBSE191.

Lawns of experimental bacteria excluding *Pectobacterium caratovorum* and *Staphylococcus aureus* among the experimental bacteria were prepared using LB medium, and lawns of *P. caratovorum* and *S. aureus* were prepared using TSA medium.

The phage lysate ($2\times10^8$ PFU) was dropped onto the lawn of each strain and then cultured at 37° C. for 24 hours, except that the cultivation was performed at 30° C. for 24 hours in case of *P. caratovorum* KACC 21701. The efficiency of plaque formation of phages was measured for *Salmonella* strains and several Gram-positive and Gram-negative strains, and the results are shown in Table 1 below. Efficiency of plating (EOP) was calculated according to the following equation, and +++ indicates greater than 1, ++ indicates 0.001 to 1, + indicates less than 0.001, and − indicates no susceptibility to phage, based on EOP:

$$\text{The efficiency of plating } (EOP) = \frac{\text{Output plaque number on targeted bacteria } (PFU/\text{mL})}{\text{Input plaque number on reference bacteria } (PFU/\text{mL})}$$

TABLE 1

| Bacterial isolate | Plaque formation[a] | Sorce or reference |
|---|---|---|
| *S. enterica* serotype Enteritidis | | |
| ATCC 13076 | +++ | ATCC |
| *S. enterica* serotype Typhimurium | | |
| ATCC 14028 | +++ | ATCC |
| KCTC 1425 | ++ | KCTC |
| ATCC 19586 | ++ | ATCC |
| ATCC 43147 | ++ | ATCC |
| NCTC 12023 | +++ | NCTC |
| SL1344 | + | NCTC |
| LT2C | +++ | (Erickson et al., 2009) |
| *S. enterica* serotype Paratyphi | | |
| A IB211 | + | IVI |
| *S. enterica* serotype *salamae* | | |
| ATCC 43972 | + | ATCC |
| *S. enterica* serotype *diarizonae* | | |
| ATCC 43974 | +++ | ATCC |
| *S. enterica* serotype Dublin | | |
| 1B 2973 | ++ | IVI |
| Collection of Gram-negative bacteria | | |
| *E. coli* O157:H7 ATCC 35150 | − | ATCC |
| *E. coli* ATCC 23724 | − | ATCC |
| *Klebsiella pneumoniae* KCTC 2242 | − | ATCC |
| *Enterococcus faecalis* ATCC 11304 | − | ATCC |
| *Vibrio parahaemolyticus* KCTC 2471 | − | KCTC |
| *Vibrio vulnificus* CMCP6 | − | IVI |
| *Shigella sonnei* KCTC 22530 | − | KCTC |
| *Shigella flexneri* KCTC 2993 | − | KCTC |
| *Pseudomonas aeruginosa* ATCC 27853 | − | ATCC |
| *Yersinia enterocolitica* ATCC 55075 | − | ATCC |
| *Cronobacter sakazakii* ATCC 29544 | − | ATCC |
| *Pectobacterium carotovorum* KACC 21701 | − | KACC |
| Collection of Gram-positive bacteria | | |
| *Staphylococcus aureus* ATCC 29213 | − | ATCC |
| *Listeria monocytogenes* ATCC 15313 | − | ATCC |
| *Bacillus cereus* ATCC 27348 | − | ATCC |

Referring to the results in Table 1, the phage PBSE191 specifically infected *Salmonella enterica*, but did not infect other strains.

Specifically, the phage has been shown to be active against a wide spectrum of *Salmonella*, including six serotypes of S. Enteritidis, S. Typhimurium, S. Paratyphi, S. Salamae, S. Diarizonae and S. Dublin.

Compared to the existing phages SS3e and BSP101, which show activity not only against *Salmonella* but also against *Shigella* or *E. coli*, the phage PBSE191 has a characteristic of specifically infecting *Salmonella* and also a characteristic capable of killing various types of *Salmonella*. Therefore, the phage PBSE191 can be expected to be usefully used in the food industry where *Salmonella* control is required.

Experimental Example 4: Phage Adsorption Analysis

The adsorption of the phage PBSE191 was evaluated using the time required for the phage to be adsorbed to the surface of the host bacteria.

An overnight culture of strain S. Enteritidis ATCC 13076 was diluted 1:100 in LB broth and cultured at 37° C. for 3 hours under aerobic conditions. After centrifugation of the cultured bacteria ($4.7\times10^8$ CFU) at 15,000×g for 1 minute, the pellet was immediately resuspended in 10 mL of fresh LB broth.

Figure 3:
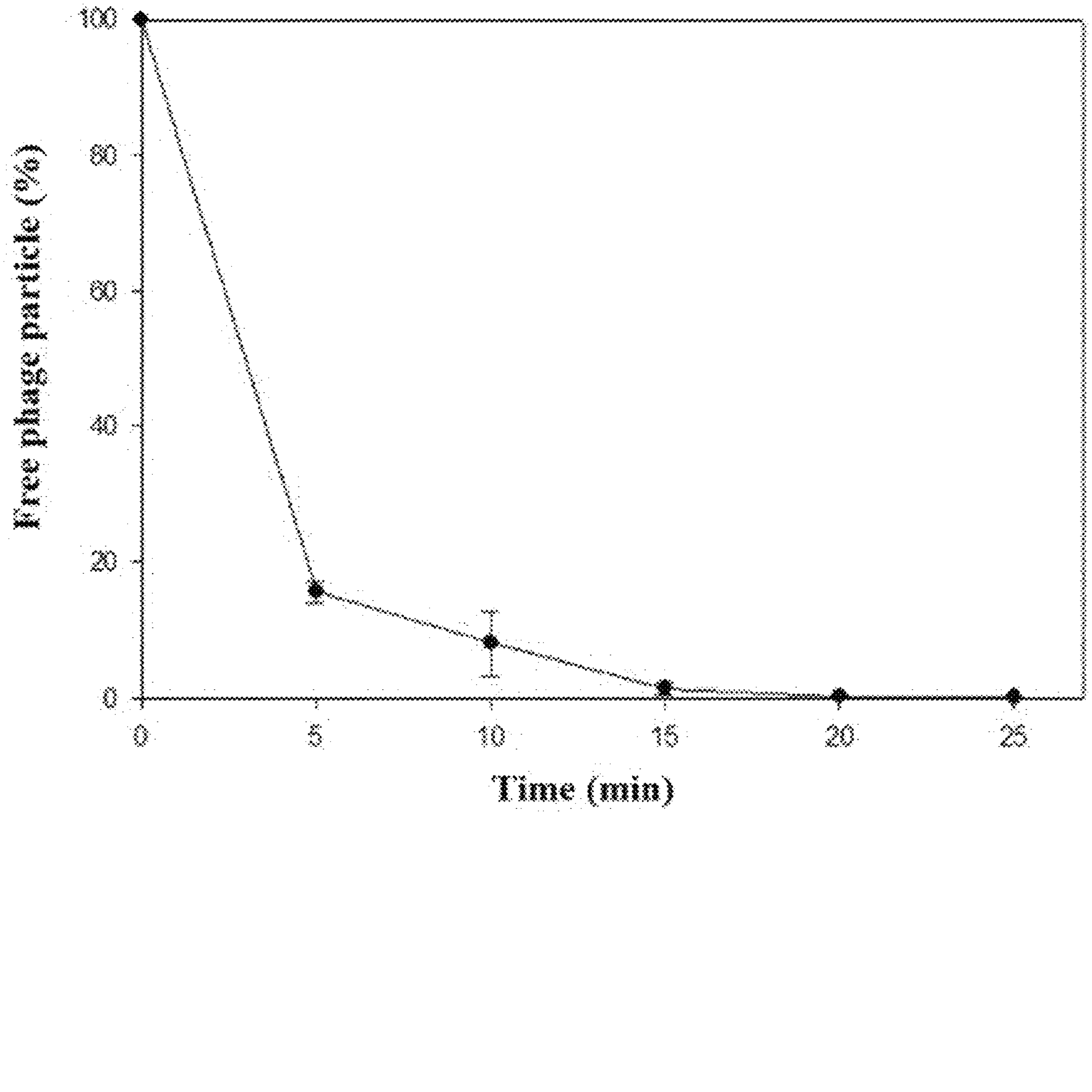
FIG. 3 shows the results of measuring the adsorption of bacteriophage PBSE191 according to an embodiment of the present invention.

Cells were infected with the phage under the condition of MOI of 0.001, 1 mL of the suspension was taken as a sample, and statically cultured at 37° C., respectively. Samples were taken after 0, 5, 10, 15, 20, 25 and 30 minutes, respectively, and then each sample was immediately centrifuged at 15,000×g for 1 minute, and then filtered. The samples were plated using a double-layer agar assay, and the phage titer was determined. The above experiment was repeated three times and the results are shown in FIG. 3. The phage adsorption can be calculated according to the following equation:

$$\text{Asorption rate } (\%) = \frac{\text{Initial phage titer} - \text{Phage titer after incubation}}{\text{Initial phage titer}} \times 100$$

Referring to FIG. 3, the results showed that 92.03% and 99.85% of the initial phage population were adsorbed to the surface of the host bacteria after 10 minutes and 25 minutes, respectively, and through this, it could be confirmed that the phage had a fast adsorption.

Experimental Example 5: One-Step Growth Analysis of Phage

In order to measure the latent period and burst size for the phage PBSE191, a one-step growth analysis was performed.

The phage and bacteria suspension were cultured at 37° C. for 25 minutes in a static state, so that the phage was adsorbed to the surface of the bacteria. After incubation, the suspension was centrifuged at 15,000×g for 1 minute, and the supernatant was subjected to a plaque assay to measure the titer of non-adsorbed phage.

Pellets containing the phage-infected host bacteria were immediately resuspended in 10 mL of LB broth and then cultured at 37° C., and 100 μl samples were collected every 10 minutes for 2 hours. The collected samples were plated on LB agar and used for phage counting through a double-layer agar technique.

The latent period (min) was confirmed by the significant increase in phage titer and the time required for the infected bacteria to lyse, and the burst size may be calculated using the following equation:

$$\text{Relative burst size } (PFU/\text{cell}) = \frac{\text{Final titer } (PFU/\text{mL}) - \text{Initial titer } (PFU/\text{mL})}{\text{Initial titer } (PFU/\text{mL})}$$

Figure 4:
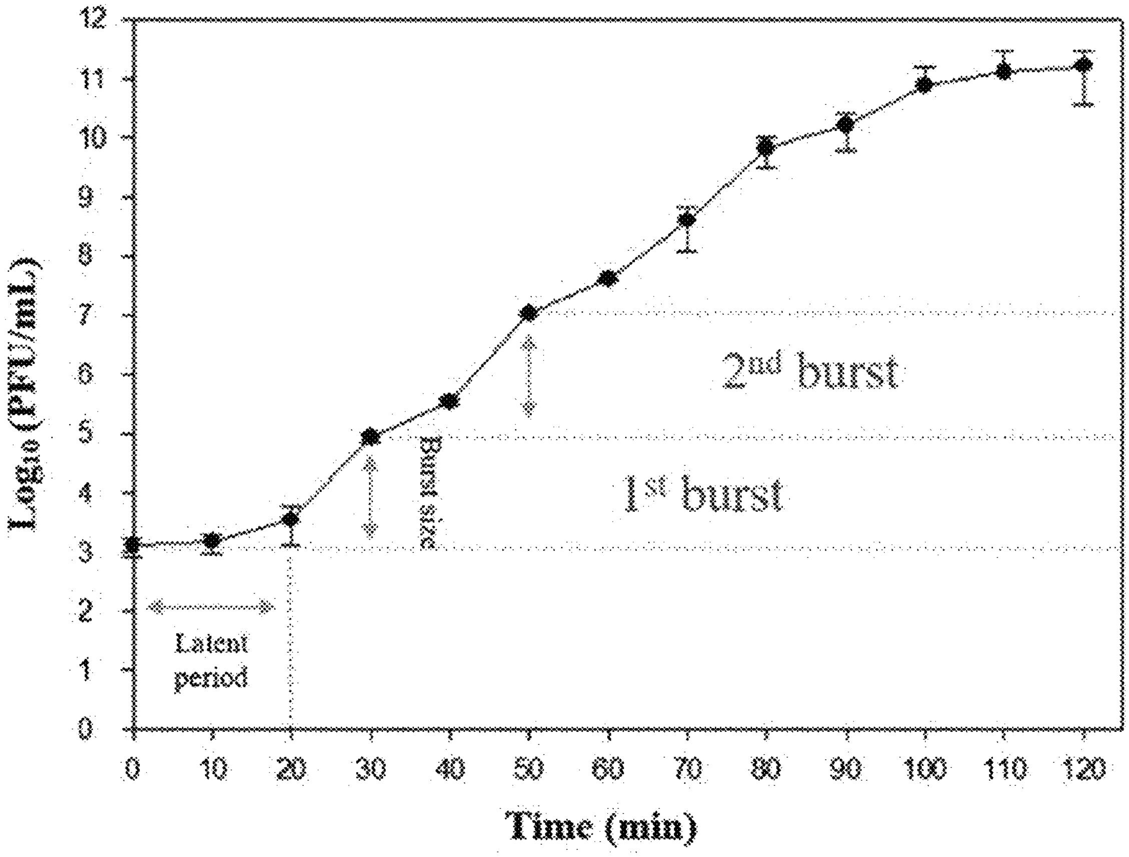
FIG. 4 shows a one-step growth curve of bacteriophage PBSE191 according to an embodiment of the present invention.

FIG. 4 shows the one-step growth curve of the phage, and referring to this, it was confirmed that when infected with S. Enteritidis, the latent period was as short as 20 minutes, and the first and second burst time points were 30 minutes and 50 minutes, respectively. In addition, the first burst size was 265 PFU/infected cell, and the second burst size was 127 PFU/infected cell. Considering that the average burst size was 112±48 PFU/infected cell (n=15) in the case of previously reported *Salmonella* phages, it can be confirmed from the above results that the phage has an excellent burst size.

Experimental Example 6: Measurement of Thermal Stability and pH Stability of Phage Stability was evaluated by measuring the survival rate of the phage PBSE191 in a wide temperature range from −18 to 80° C. and a pH range of 1 to 9.

Figure 5:
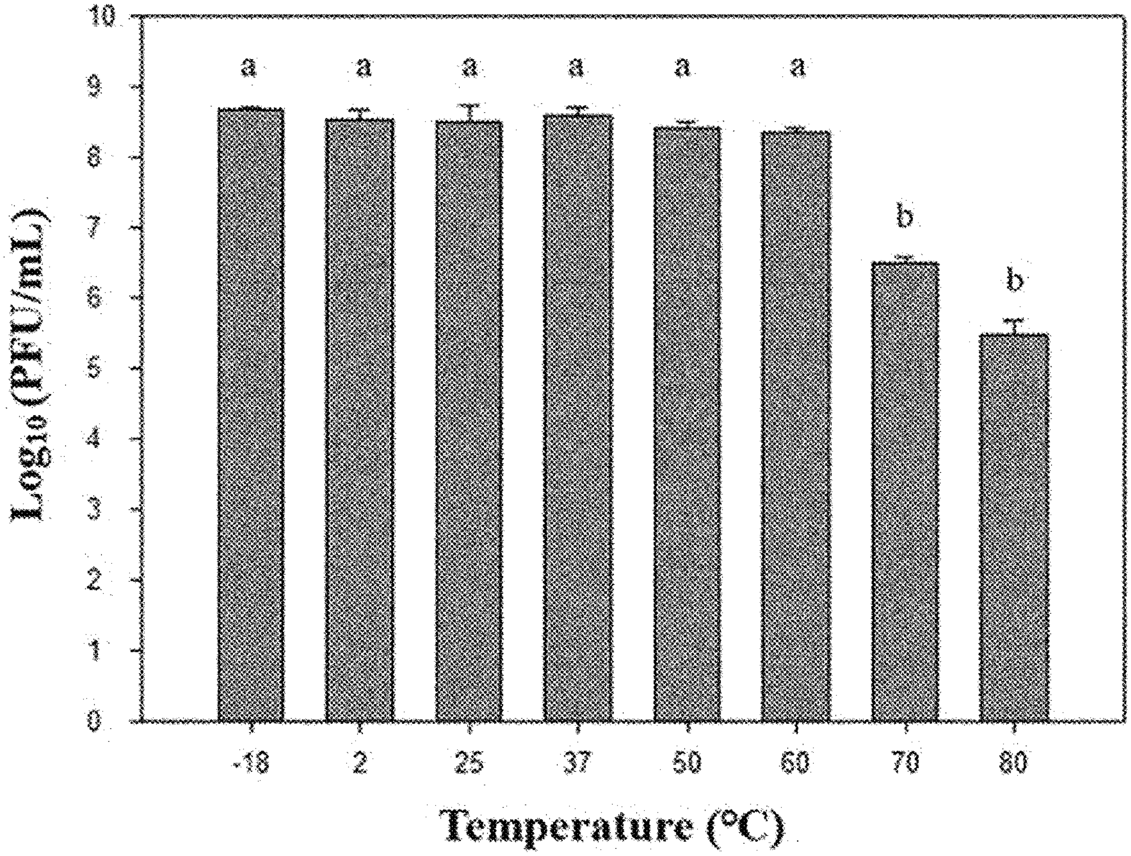
FIG. 5 is a graph showing the results of measuring the survival rate in the range of −18 to 80° C. for bacteriophage PBSE191 according to an embodiment of the present invention.
Figure 6:
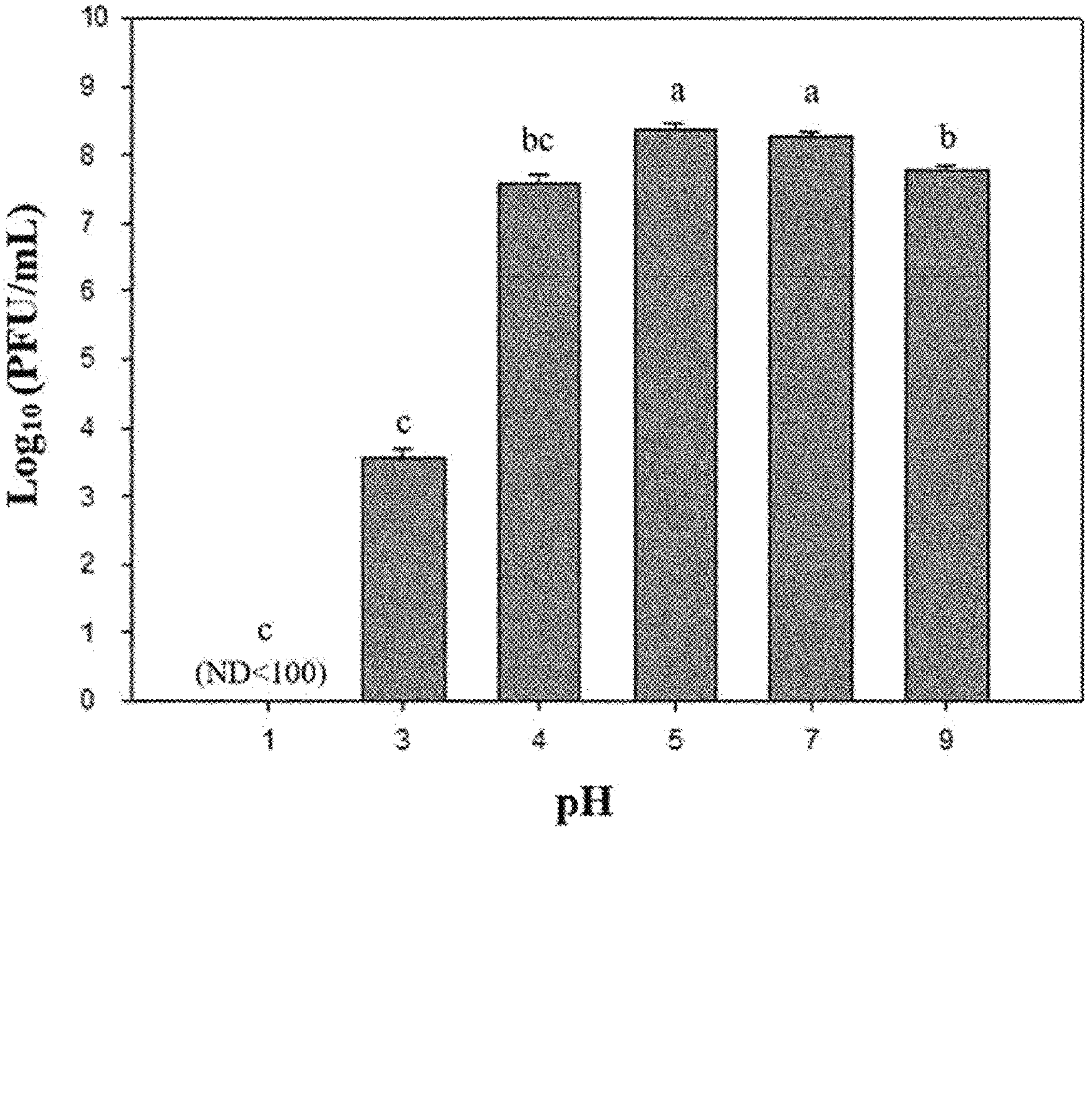
FIG. 6 is a graph showing the results of measuring the survival rate in the range of pH 1 to 9 for bacteriophage PBSE191 according to an embodiment of the present invention.

For the measurement of thermal stability, phage lysates ($10^8$ PFU) were cultured for 30 minutes at different temperatures ranging from −18 to 80° C. For the measurement of pH stability, phage lysates ($2\times10^8$ PFU) were cultured for 30 minutes in buffers of various pHs (pH 2-9). The remaining phages were counted by plating, and the experiment was repeated three times, and then the results of the experiment are shown in FIGS. 5 and 6, respectively. Phage stability may be calculated according to the following equation:

$$\text{Phage stability } (\%) = \frac{\text{Surviving phage titers after treatment } (PFU/\text{mL})}{\text{Phage titer before treatment } (PFU/\text{mL})} \times 100(\%)$$

Referring to the results of the thermal stability test in FIG. 5, it was confirmed that as a result of culture at −18° C. to 60° C. for 30 minutes, the survival rate of the phages was not significantly affected. On the other hand, it was affected at the temperature of 70° C. and 80° C., but it was confirmed that more than 5 log PFU/mL of phages remained even after treatment for 30 minutes. These results were similar to those of phages LSE7621, LPST10 and vB_SalP_TR2, and the survival rate is superior to that of phages SE-P3, SE-P16, SE-P37 and SE-P47 at 80° C.

According to the results of the pH stability test in FIG. 6, the phages stably survived even after culture in the pH range of 5 to 7 for 30 minutes. Optimal stability was observed by a phage reduction of less than 1 log PFU/mL in the pH range of 4 to 9, and phages were inactivated at pH 1, but more than 3.5 log PFU/mL of phages survived even after treatment at pH 3 for 30 minutes.

These results are comparable to phage SS3e, and it could be confirmed that the phage PBSE191 exhibited stability in a wide range of temperature and pH conditions, and accordingly could be usefully used in food and food manufacturing.

Experimental Example 7: Analysis of Host Bacterial Receptors of Phage

Receptor analysis of the phage PBSE191 was performed using S. Typhimurium LT2C as host bacteria.

ΔrfbP/LT2C knock-out mutants and their complemented strains (ΔrfbP complemented with pUHE::rfbP/LT2C plasmid) were provided and used from the Seoul National University laboratory.

Wild-type bacteria and the knock-out mutants were cultivated overnight in LB broth, and then the complemented strains were cultured in LB broth containing carbenicillin at 37° C. under aerobic conditions. In order to identify the phage receptor, spotting assay was performed with wild type, ΔrfbP/LT2C mutants and ΔrfbP complemented strains, and the results are shown in FIG. 7.

Figure 7:
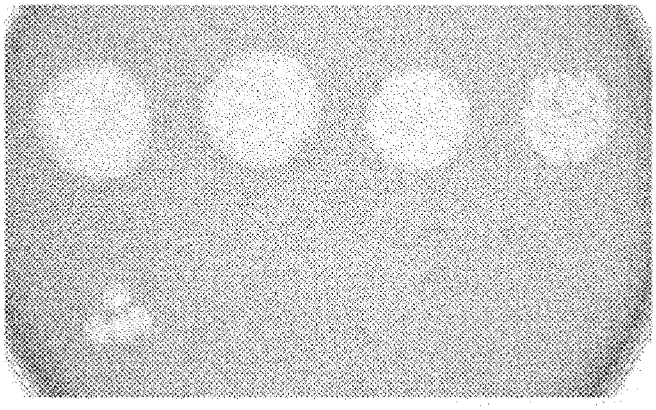
FIG. 7 shows a picture of a spot test experiment for analyzing the receptor of bacteriophage PBSE191 according to an embodiment of the present invention.
Figure 7:
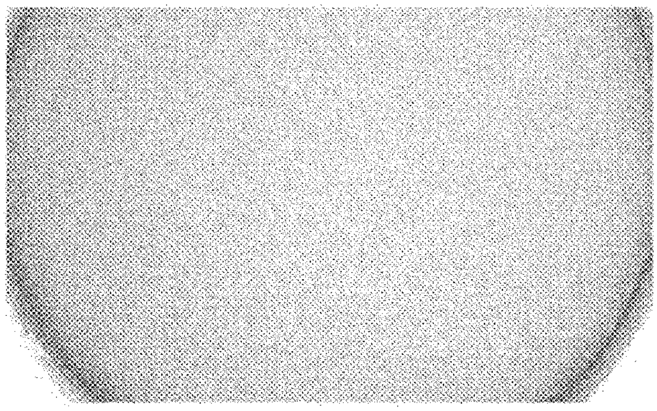
Figure 7:
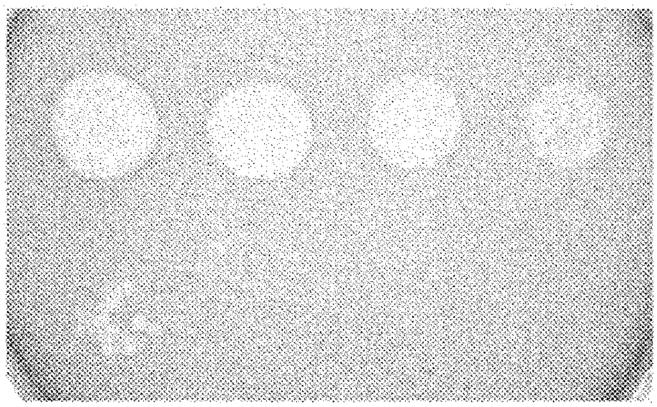

Referring to FIG. 7, S. Typhimurium ΔrfbP/LT2C mutants exhibited resistance to the phage, and as a result of complementing the strain with rfbP, the results showed that phage sensitivity was recovered.

These results indicate that the phage PBSE191 recognizes the O-antigen of *Salmonella* lipopolysaccharide (LPS) as a host bacterial receptor.

Experimental Example 8: Analysis of Phage DNA

Purification of Phage DNA

DNA of the phage PBSE191 was purified using a standard phenol-chloroform extraction method.

Before purification, 500 μl of phage lysates were treated with 1 μl/mL of DNase I and 1 μl/mL of RNase I at room temperature for 30 minutes to remove bacterial DNA and RNA contaminants. Then, the phage lysates were treated with lysis buffer containing 0.5% sodium dodecyl sulfate (SDS), 0.5 M EDTA (pH 8.0) and 50 μl/mL of proteinase K, and the mixture was cultured at 65° C. for 15 minutes.

Thereafter, phenol was added to extract phage DNA, and the mixture was centrifuged at 5,000 rpm for 5 minutes at room temperature. Next, the aqueous layer was carefully mixed with a phenol-chloroform-isoamyl alcohol (25:24:1) solution, and then centrifuged at 5,000 rpm for 5 minutes to remove unnecessary components such as polysaccharides and protein components. Then, the same steps were repeated with chloroform.

The aqueous layer was collected with 3 M sodium acetate (NaOAc, pH 5.2), and then ethanol precipitation was performed. Finally, purified phage genetic DNA was stored in TE buffer and used in experiments.

Genetic Sequencing and Biological Information Analysis

The open reading frame (ORF) of the phage genome was identified using the RAST (rast.nmpdr.org/), GeneMarkS (exon.gatech.edu/GeneMark/genemarks.cgi) and FgenesV (trained Pattern Markov chain-based viral gene prediction software) programs. For the unknown ORF, the non-overlapping protein NCBI database (blast.ncbi.nlm.nih.gov/) using BLASTP and the homologous ORF of other existing bacteriophages were referred to ORF inference.

Figure 8:
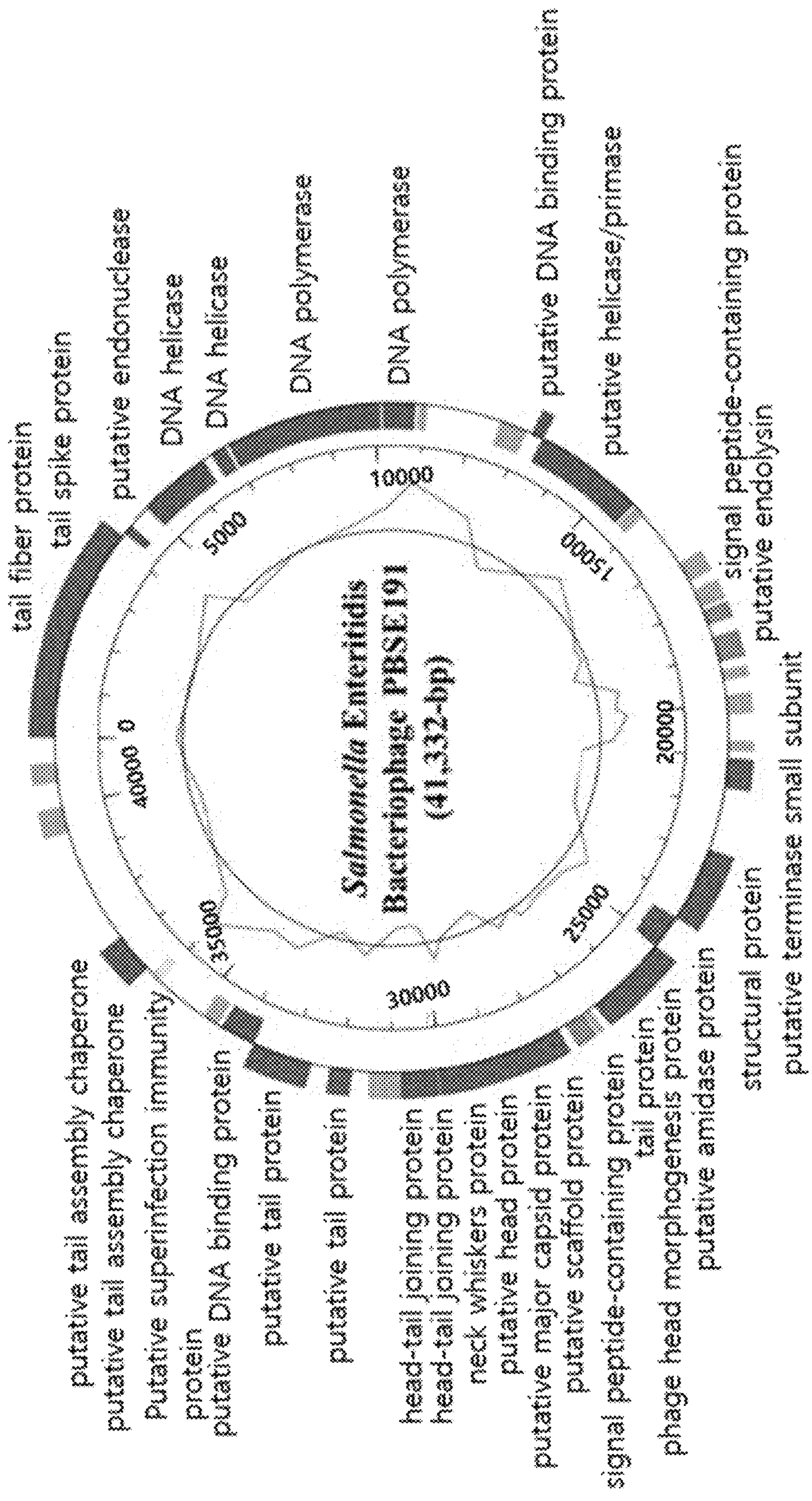
FIG. 8 shows a genome map of bacteriophage PBSE191 identified in an embodiment of the present invention.

Based on the analysis results, a genome map was created using Genescene software (DNAstar, Madison, WI) and shown in FIG. 8. The genome sequence of the phage was registered with GenBank under Accession No. OM291373 (nobi.plm.nih.&c re/OM291373). As a result of the analysis, it was inferred that the genome of the phage PBSE191 is composed of 41,332 bp, of which the GC content is 49.84%, and encodes 43 ORFs.

As a result of confirming the ORF, it was confirmed that the phage did not have lysogeny module genes such as cro, cl, and integrase or toxic genes, and through this, the safety of the phage could be confirmed.

Figure 9:
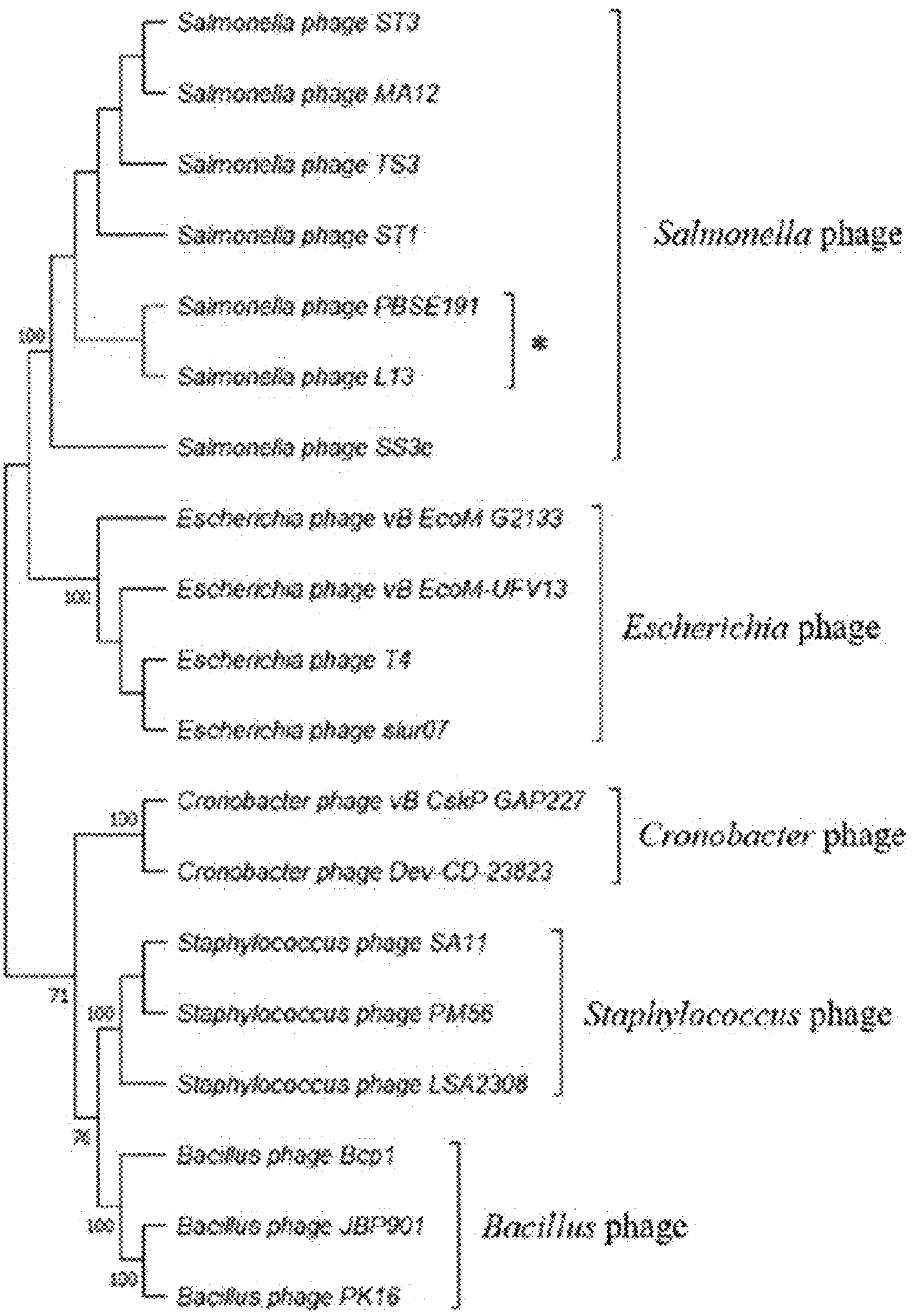
FIG. 9 shows the phylogenetic tree of bacteriophage PBSE191 identified in an embodiment of the present invention.

For phylogenetic confirmation of the phage, a phylogenetic analysis based on major capsid protein (ORF29) was performed by a neighbor-joining method in which bootstrap was repeated 2,000 times using Molecular Evolutionary Genetics Analysis 11 (MEGA 11) software, and a phylogenetic tree was shown in FIG. 9. In FIG. 9, those closely related on the phylogenetic tree are marked with *.

As a result of phylogenetic analysis, the major capsid protein of phage PBSE191 was similar to the major capsid protein of phages L13, SS3e and TS3, and through this, it was confirmed that it belongs to the *Salmonella* phage family.

Preparative Example 2: Preparation of PVA Film Using Phage

Using the phage PBSE191, a polyvinyl alcohol (PVA) film with the phage was prepared. PVA purchased from Sigma-Aldrich was used, and the weight average molecular weight of the PVA was 13,000 to 23,000, and the degree of saponification was 87 to 89%. A 11 g/100 mL PVA solution was prepared using distilled water, and then sorbitol (D-sorbitol 97%), glycerol (99%) or trehalose (D-(+)-trehalose dihydrate), which is used as a plasticizer and a wetting agent, was added to the 11% PVA solution at concentrations of 0%, 10% and 20% (w/w) based on the weight of PVA, and then heated to 80° C. while stirring for 60 minutes.

Upon complete dissolution, the solution was sterilized by autoclaving at 121° C. for 15 minutes. The autoclaved solution was cooled to room temperature, and to the prepared solution a PBS-based phage lysate ($10^{10}$ PFU) was added at a volume ratio of 9:1, and then mixed uniformly and degassed. The film solution of the control group was prepared by mixing 11% autoclaved PVA solution with sterilized PBS buffer at a volume ratio of 9:1.

1 mL of each solution was poured into a Petri dish and dried for 15 hours under conditions of 25° C. and 50 RH % in a hygro-thermostat. The dried film was removed from the casting surface and used for experiments.

Figure 10:
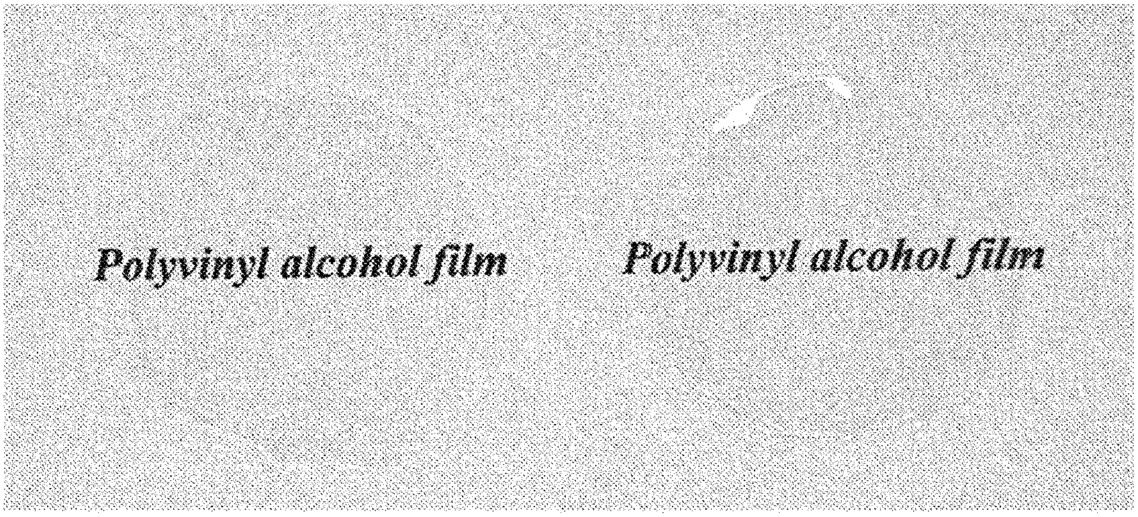
FIG. 10 is a picture showing a comparison of the film with bacteriophage PBSE191 prepared according to an embodiment of the present invention compared to a film without bacteriophage.

FIG. 10 shows photographs of a film without phage (left) and a film with phage (right), with respect to a film containing 10% PVA and 2% sorbitol (w/w). Referring to the drawing, it can be seen that there is no significant difference in appearance depending on whether phages are contained or not.

Experimental Example 9: Analysis of Phage Viability on Film

In order to confirm the survival rate of phages in a PVA film containing glycerol (G), sorbitol (S) or trehalose (T) as a plasticizer, the material was added in an amount of 10 or 20% by weight based on the PVA weight according to the method of Preparative Example 2 to prepare a PVA film. The initial phage titer of each film solution was set to $4\times10^9$ PFU/mL.

The prepared film was dissolved in 10 mL of PBS buffer at 20° C. and 200 rpm for 30 minutes, and the survival rate of phage was evaluated using a double-layer plaque assay. The surviving phages were counted, and the results of measuring phage viability in the PVA film with phage containing each plasticizer are shown in FIG. 11.

Figure 11:
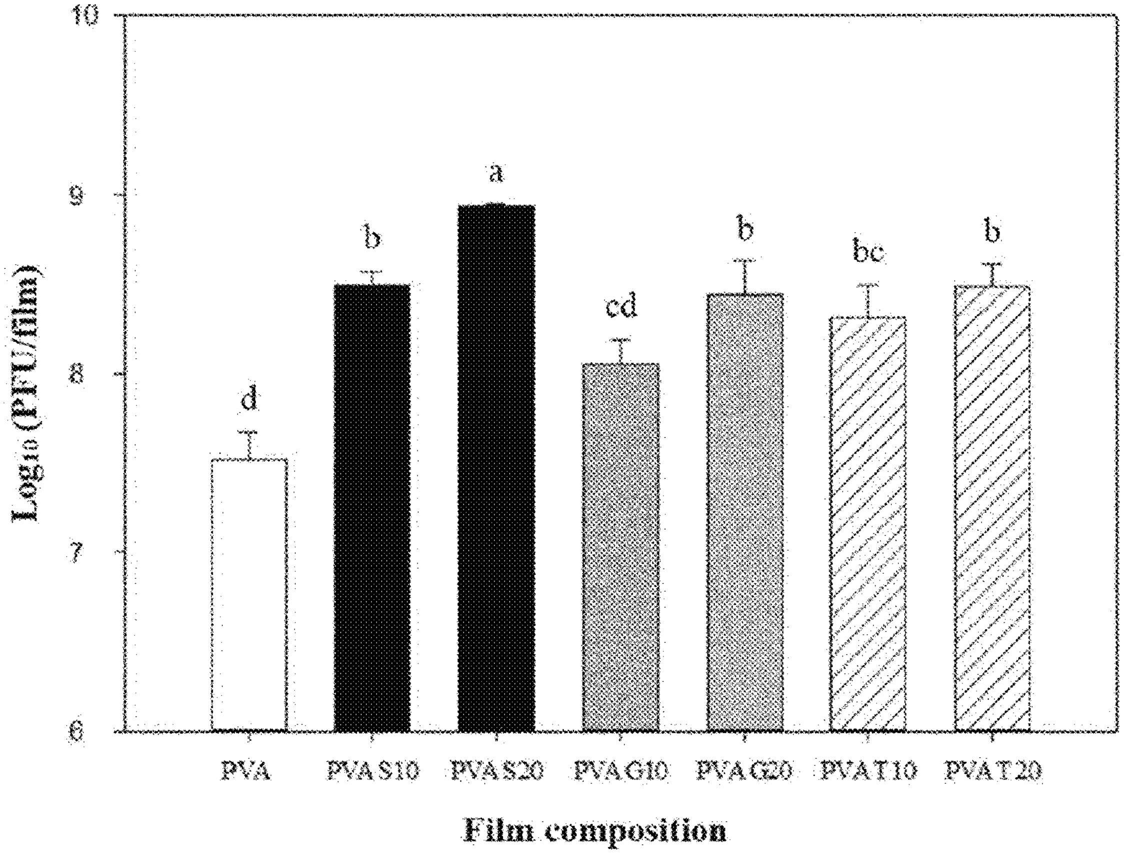
FIG. 11 is a graph showing the results of comparing the survival rate of bacteriophage according to the type and content of the plasticizer in the film with bacteriophage PBSE191 prepared according to an embodiment of the present invention.

According to the results of FIG. 11, it can be seen that 2 log PFU or more of phage are inactivated in the 10% (w/v) PVA film without plasticizer, whereas the viability of the phage is improved in the film containing sorbitol, glycerol or trehalose, and in particular, sorbitol exhibited superior activity in terms of phage protection compared to other wetting agents.

Specifically, most of the phage particles survived in 20% sorbitol, and inactivated phage were less than 0.5 log PFU. On the other hand, 1.1, 1.1, 1.3, 1.1 and 1.2 log PFU of phages were inactivated in 10% sorbitol, 20% glycerol, 10% glycerol, 20% trehalose and 10% trehalose, respectively. From this, it was confirmed that the survival rate of phage was the best in the film (PVAS20) using 20% sorbitol in the 10% (w/v) PVA film.

Experimental Example 10: Confirmation of Phage Stability on PVA Film

For the PVAS20 film with phage, the phage stability of was confirmed for 30 days.

The PVAS20 film with phage was dissolved in 10 mL of PBS buffer at 20° C. and 200 rpm for 30 minutes, and the survival rate of the phage was evaluated using a double-layer plaque assay. In this way, the phage stability on the film was tested every 1, 3, 10, 20 and 30 days for 30 days.

The surviving phages were counted by plating, and the experiment was repeated three times.

Figure 12:
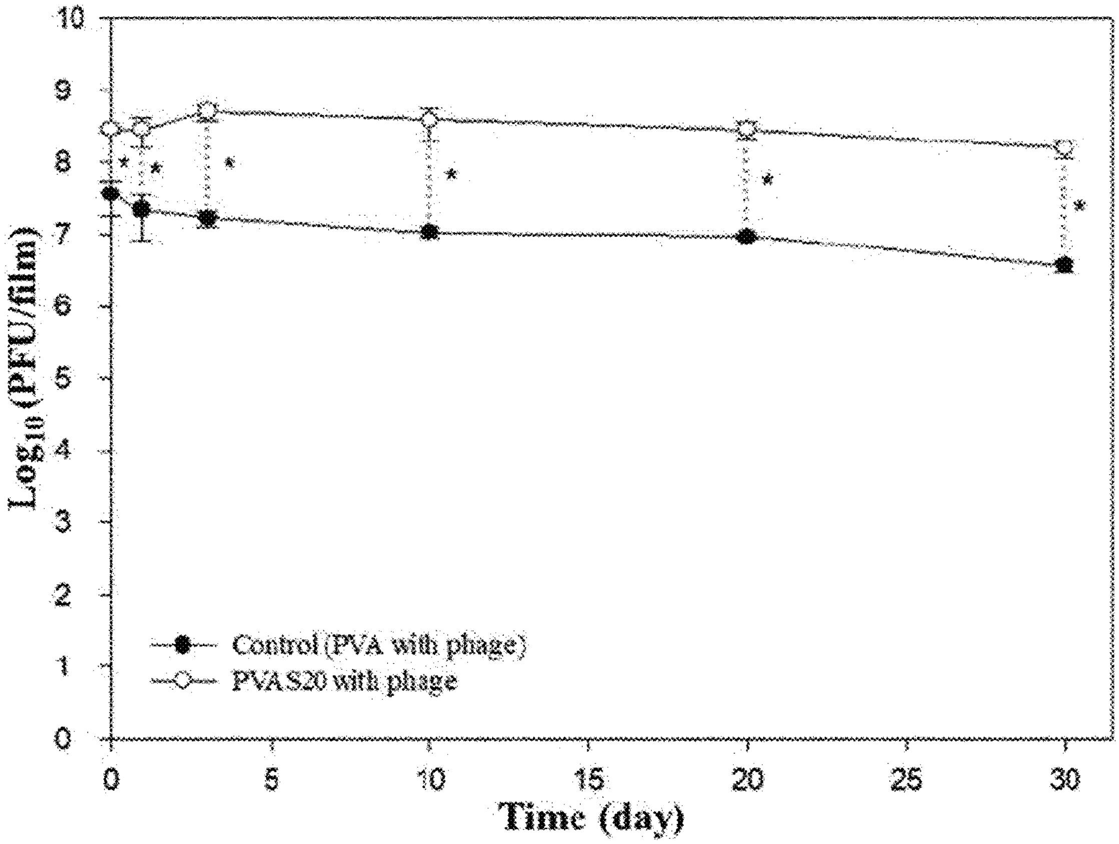
FIG. 12 shows the results of measuring the bacteriophage stability in the film with bacteriophage PBSE191 prepared according to an embodiment of the present invention.

FIG. 12 shows the results of measuring the phage stability on the PVA film. Referring to FIG. 12, it can be surprisingly confirmed that the phage exhibited excellent survival rate for 30 days under dry conditions, and through this, it could be seen that the phage was successfully protected and preserved in the PVA polymer matrix.

Experimental Example 11: Confirmation of Antibacterial Activity of PVA Film with Phage For the PVAS20 film with phage, antibacterial activity against *Salmonella* bacteria was tested.

To measure the antibacterial activity, 10 mL of S. Enteritidis ATCC 13076 cell suspension (about $10^5$ CFU/mL, early-exponential phase) in LB broth was prepared. Thereafter, the film was immersed in the suspension while shaking at 200 rpm for 4 hours at 37° C. The amount of phage in the film was about $10^8$ PFU/film, and a film without phage was used as a control group. Antibacterial activity was measured at 0.5, 1, 2 and 4 hours, and the results are shown in FIG. 13.

Figure 13:
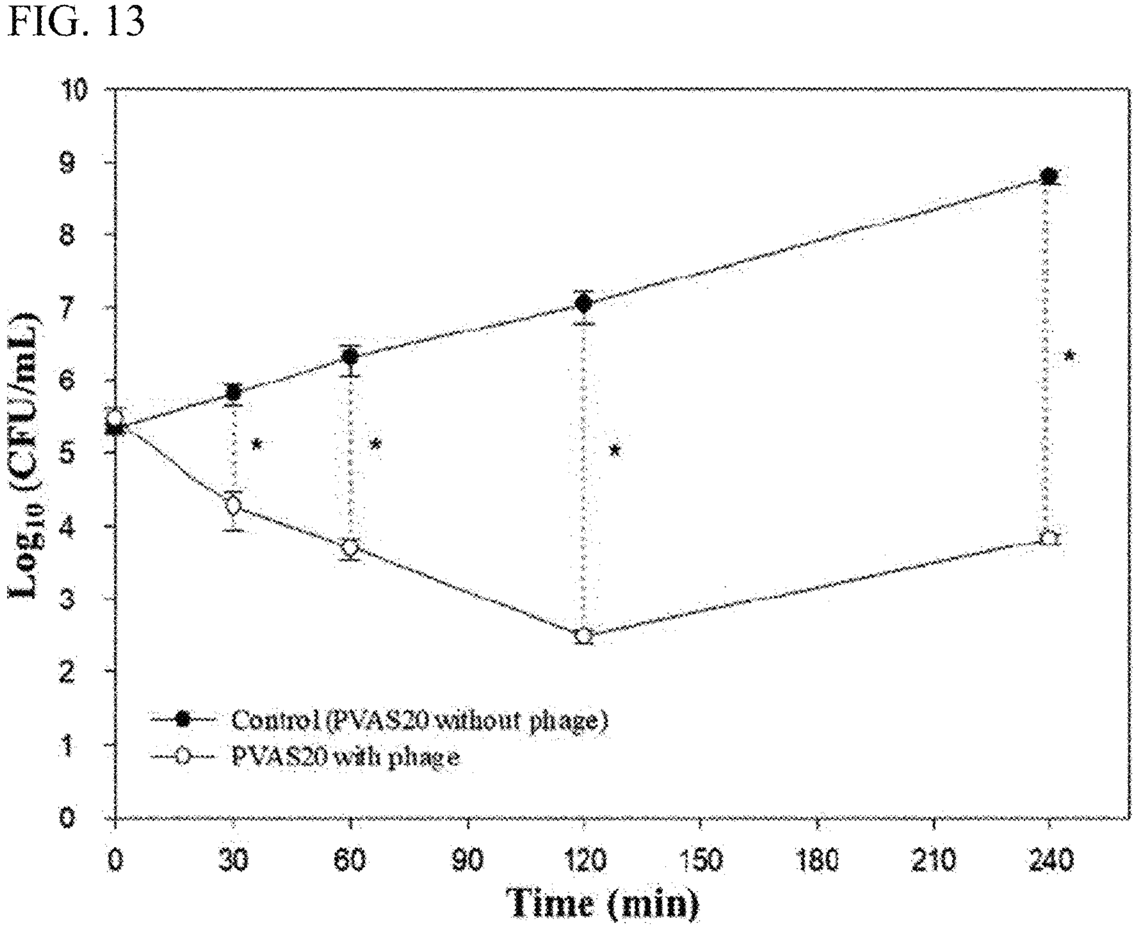
FIG. 13 shows the results of measuring the antibacterial activity of bacteriophage in the film with bacteriophage PBSE191 prepared according to an embodiment of the present invention.

According to FIG. 13, it was shown that the phage particles in the film maintained the host lytic activity against S. Enteritidis for 4 hours. Through this, it could be confirmed that the phage could continuously exhibit antibacterial activity in the PVAS20 film with phage.

Experimental Example 12: Measurement of Antibacterial Activity of PVA Coating with Phage In order to evaluate the antibacterial activity of the coating with phage, egg shell samples (0.46±0.05 g, n=125) with a particle diameter of 2.5 cm were prepared using an egg opener (Guangzhou Le Tian Pen Co., Ltd., China), and sterilized by autoclaving at 121° C. for 15 minutes. Next, 54 clean egg shells were randomly divided into 3 groups (control group, PVAS20 coating group without phage, and PVAS20 coating group with phage).

The subcultured S. Enteritidis was cultured at 37° C. for 1.5 hours (early exponential phase) under aerobic conditions. The culture was centrifuged at 15,000×g for 1 minute, and the bacterial pellet was resuspended in 100 μl of LB broth. Egg shell surface was spot inoculated with 10 μl of bacterial cells with $2.4\times10^8$ CFU/mL and allowed to air dry at room temperature for 30 minutes.

For the phage-coated group, the inoculated egg shells were immersed in a PVAS20 coating solution with phage ($4.0\times10^9$ PFU/mL) for 3 seconds and then dried at room temperature for 40 minutes. For the control group, egg shells were either uncoated, or immersed in a PVAS20 coating solution without phage and dried for 40 minutes. Six egg shell samples were selected from each group and stored for 24 hours under conditions of 5° C. and 50% relative humidity, and then tested for antibacterial activity against *Salmonella.*

For the antibacterial activity test, the samples were homogenized with 10 ml of sterile PBS buffer for 30 seconds using Pulsifier II (Microgen Bioproducts Ltd., UK). All samples were diluted 10-2 and plated on XLD agar (MB-X1060; MB cell, Seoul, Korea), and then cultured at 37° C. for 24 hours. The number of black colonies was counted by plating, and the titer of the phages remaining on the coated egg shells was measured by the double-layer agar assay.

Figure 14:
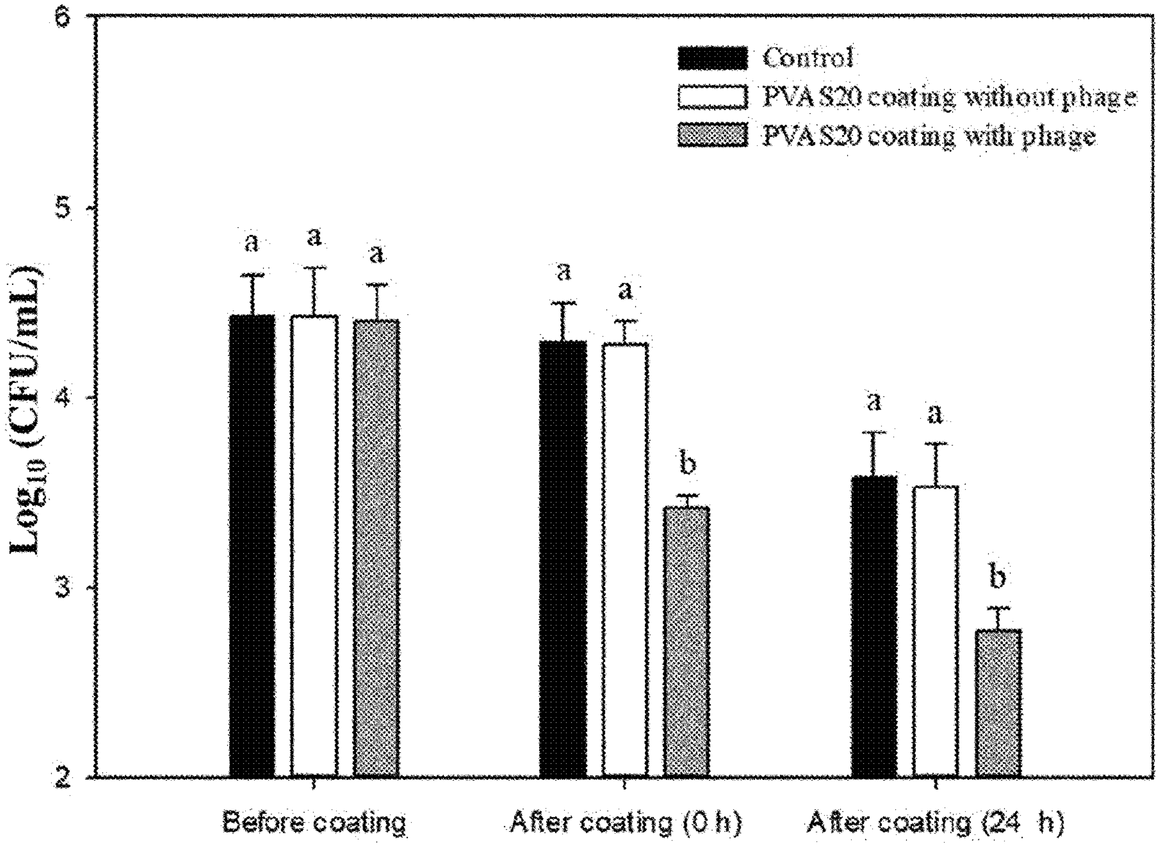
FIG. 14 shows the results of measuring the antibacterial activity before and after coating in the coating with bacteriophage PBSE191 prepared according to an embodiment of the present invention.

FIG. 14 shows the results of measuring S. Enteritidis cells before coating, immediately after coating, and after 24 hours of coating. Referring to FIG. 14, it can be confirmed that a significant amount of *Salmonella* (about 1 log CFU) bacteria was killed at room temperature immediately after the PVAS20 coating with phage is formed on the egg shells. It was confirmed that a cell reduction of about 2 log CFU was induced after 24 hours compared to the initial inoculation amount in the case of the PVAS20 coating with phage, whereas the reduction was about 1 log CFU in the case of the control group.

From the above results, it was confirmed that in the case of the PVAS20 coating with phage, the phages could contact the bacteria and induce their death during the drying step (40 minutes) after coating. In addition, it was confirmed that the reduction in the number of bacteria continued even after 24 hours, as the phages survived for a long time in the PVAS20 coating and continuously exhibited the effect.

Accordingly, it could be confirmed that the PVA coating with phage exhibited excellent stability and antibacterial activity when applied to the egg shells.

Although some embodiments of the present invention have been described above, it should be understood that the present invention is not limited only to the embodiments as described above, but modifications and variations may be implemented within the scope not departing from the gist of the present invention, and such modifications and variations are also included in the technical spirit of the present invention.

What is claimed is:

1. A coating composition comprising a bacteriophage having a bactericidal activity against *Salmonella* spp. bacteria, a polymeric compound, and a plasticizer, wherein the bacteriophage is a bacteriophage deposited at the Korean Collection for Type Culture (KCTC) under accession no. KCTC14929BP, having a bactericidal activity against *Salmonella* spp. bacteria.

2. The coating composition according to claim 1, wherein the *Salmonella* spp. bacteria comprise *Salmonella enterica.*

3. The coating composition according to claim 1, wherein the *Salmonella* spp. bacteria include one or more *Salmonella enterica* serotypes selected from the group consisting of *Salmonella* Enteritidis (S. Enteritidis), *Salmonella* Typhimurium (S. Typhimurium), *Salmonella* Paratyphi (S. Paratyphi), *Salmonella* Salamae (S. Salamae), *Salmonella* Diarizonae (S. Diarizonae), and *Salmonella* Dublin (S. Dublin).

4. The coating composition according to claim 1, wherein the polymeric compound comprises one or more selected from the group consisting of polyvinyl alcohol (PVA), polylactic acid (PLA), polycaprolactone (PCL), polybutylene succinate (PBS), polyethylene terephthalate (PET), polybutylene terephthalate (PBT), polyethylene (PE), polypropylene (PP), polyvinyl chloride (PVC), polyamide (PA), and polyurethane (PU).

5. The coating composition according to claim 1, wherein the polymeric compound comprises a biodegradable polymer.

6. The coating composition according to claim 1, wherein the plasticizer comprises one or more selected from the group consisting of sorbitol, glycerol, trehalose, fructose, sucrose, mannitol, propylene glycol, and polyethylene glycol.

7. The coating composition according to claim 1, wherein the plasticizer is in an amount of 10 to 30% by weight based on a weight of the polymeric compound.

8. The coating composition according to claim 1, further comprising a solvent.

9. The coating composition according to claim 1, wherein the bacteriophage is in an amount of $1\times10^8$ to $1\times10^{12}$ PFU/mL based on a total volume of the coating composition.

10. The coating composition according to claim 1, wherein the polymeric compound is in an amount of 5 to 20 g/100 mL based on a total volume of the coating composition.

11. The coating composition according to claim 1, wherein the plasticizer is in an amount of 1 to 5 g/100 mL based on a total volume of the coating composition.

12. An antibacterial film prepared using a coating composition comprising a bacteriophage having a bactericidal activity against *Salmonella* spp. bacteria, a polymeric compound, and a plasticizer, wherein the bacteriophage is a bacteriophage deposited at the Korean Collection for Type Culture (KCTC) under accession no. KCTC14929BP, having a bactericidal activity against *Salmonella* spp. bacteria.

13. The antibacterial film according to claim 12, wherein the antibacterial film is prepared by coating the coating composition on a substrate and drying it at a temperature of 20 to 30° C. for 10 to 20 hours.

14. The antibacterial film according to claim 12, wherein the antibacterial film is prepared by coating the coating composition on a subject to be coated and then drying it at a temperature of 20 to 30° C. for 10 to 180 minutes.

15. The antibacterial film according to claim 12, wherein the antibacterial film is a film for food packaging.

16. An antibacterial composition comprising a bacteriophage deposited at the Korean Collection for Type Culture (KCTC) under accession no. KCTC14929BP, having a bactericidal activity specifically against *Salmonella* spp. bacteria, a polymeric compound, and a plasticizer, wherein the polymeric compound is in an amount of 5 to 20 g/100 mL based on a total volume of the antibacterial composition; and wherein the plasticizer is in an amount of 1 to 5 g/100 mL based on the total volume of the antibacterial composition.

* * * * *